(12) United States Patent
Nissen et al.

(10) Patent No.: US 8,001,636 B2
(45) Date of Patent: *Aug. 23, 2011

(54) APPARATUS AND METHOD TO POSITION A PATIENT FOR AIRWAY MANAGEMENT AND ENDOTRACHEAL INTUBATION

(75) Inventors: Mark D. Nissen, Edina, MN (US); James M. Gayes, Minnetonka, MN (US)

(73) Assignee: Nissen IPAD, LLC, Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/780,615

(22) Filed: May 14, 2010

(65) Prior Publication Data
US 2010/0218316 A1 Sep. 2, 2010

Related U.S. Application Data

(63) Continuation of application No. 11/353,434, filed on Feb. 14, 2006, now Pat. No. 7,716,763.

(60) Provisional application No. 60/653,592, filed on Feb. 16, 2005, provisional application No. 60/740,086, filed on Nov. 28, 2005.

(51) Int. Cl.
*A47C 20/00* (2006.01)

(52) U.S. Cl. ........................ 5/644; 5/645; 5/654; 5/655.3

(58) Field of Classification Search .............. 5/645, 644, 5/654, 655.3
See application file for complete search history.

(56) References Cited

U.S. PATENT DOCUMENTS

| | | |
|---|---|---|
| 2,896,227 A | 7/1959 | Reed |
| 4,685,163 A | 8/1987 | Quillen et al. |
| 4,829,614 A | 5/1989 | Harper et al. |
| 5,068,933 A | 12/1991 | Sexton |
| 5,086,529 A | 2/1992 | DeGroot |
| 5,184,365 A | 2/1993 | Stafford et al. |
| 5,528,783 A | 6/1996 | Kunz et al. |
| 5,745,937 A | 5/1998 | Weismiller et al. |
| 5,809,597 A | 9/1998 | Shaw |
| 5,848,450 A | 12/1998 | Oexman et al. |
| 5,966,762 A | 10/1999 | Wu et al. |
| 6,751,818 B2 | 6/2004 | Troop |
| 2002/0040501 A1 | 4/2002 | Sharrock et al. |
| 2003/0098026 A1 | 5/2003 | Saied |

*Primary Examiner* — Michael Trettel
*Assistant Examiner* — William Kelleher
(74) *Attorney, Agent, or Firm* — Fredrikson & Byron, P.A.

(57) ABSTRACT

An apparatus and method for properly positioning a patient to allow rapid and effective endotracheal intubation during an anesthetic induction is disclosed. The apparatus includes a plurality of inflatable sections for supporting the patient's head and upper back, where the inflatable sections are independently inflatable and deflatable with respect to one another so that the patient's ear and sternum can be aligned in the same horizontal plane. The apparatus also includes an anchoring means that is attached to at least one of the plurality of inflatable sections for anchoring the apparatus in place. An air system connected to the plurality of inflatable sections and including separate connections to the individual inflatable sections operates to provide air to the apparatus. The apparatus optionally includes an independently inflatable cylinder in the anchoring means that is used in pregnant patients.

12 Claims, 6 Drawing Sheets

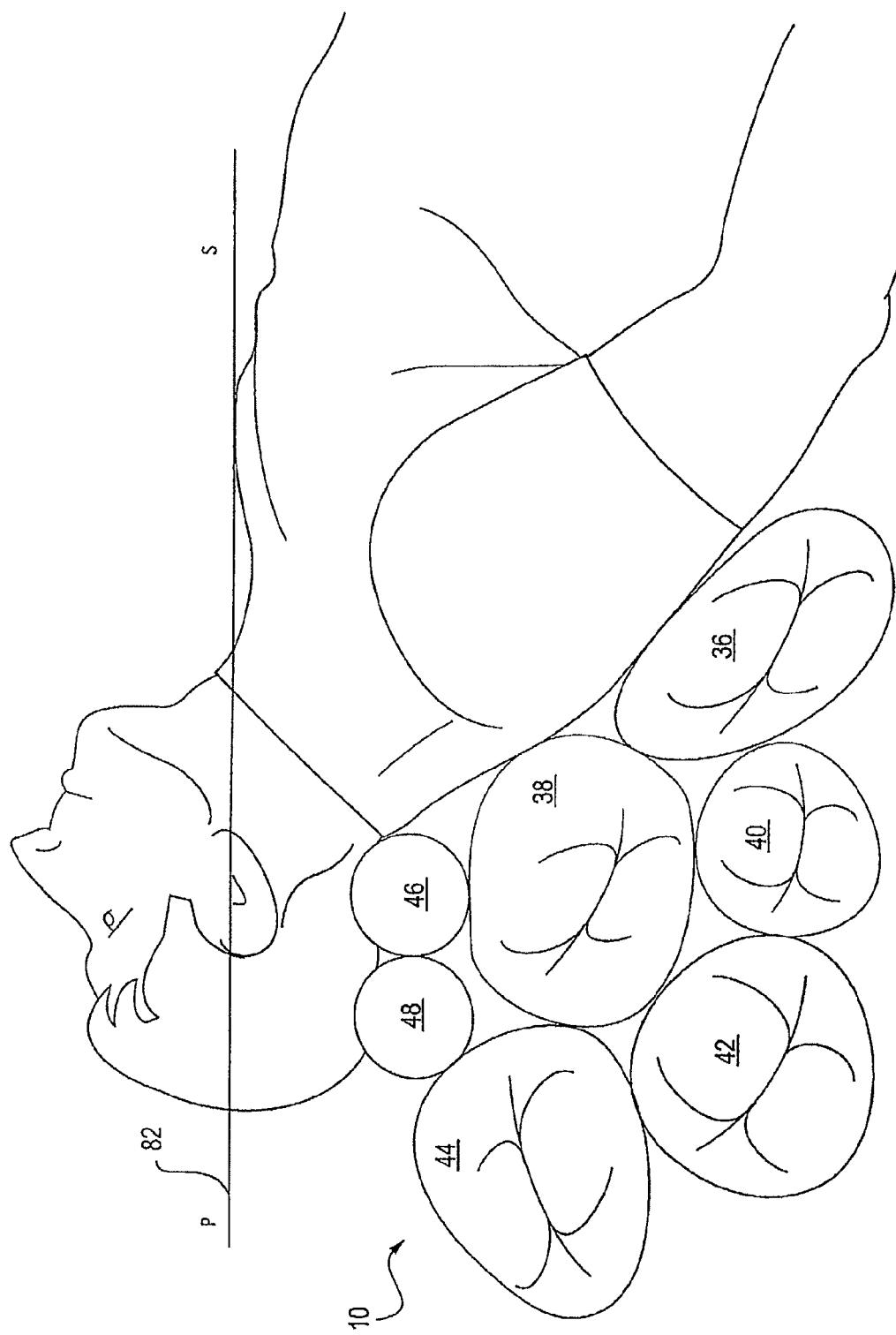

APPARATUS AND METHOD TO POSITION A PATIENT FOR AIRWAY MANAGEMENT AND ENDOTRACHEAL INTUBATION

CROSS REFERENCE TO RELATED APPLICATIONS

This application is a continuation of U.S. patent application Ser. No. 11/353,434, filed Feb. 14, 2006, now allowed, which claims the benefit of U.S. Patent Application Ser. Nos. 60/653,592 filed Feb. 16, 2005, and 60/740,086, filed Nov. 28, 2005.

BACKGROUND OF THE INVENTION

1. Field of the Invention

The present invention relates to an inflatable pillow configured to facilitate the alignment of the oropharyngeal, laryngeal, and tracheal axes of the airway of an individual in the supine position prior to induction of anesthesia and placement of an endotracheal tube. The present invention also relates to a modification of the inflatable pillow to provide left lateral tilt of the uterus as well as facilitating endotracheal intubation in pregnant patients undergoing a Cesarean section.

2. Background of the Related Art

Obesity is an epidemic in the United States and is a leading cause of morbidity and premature mortality. It is estimated that 300,000 deaths a year are related to obesity and close to $100 billion are spent on obesity-related health care costs. Obesity is a chronic condition associated with several comorbid disorders such as hypertension, diabetes, heart disease, and sleep apnea. In the United States, the prevalence has been increasing over the past several decades and in recent published US data (1999 to 2000), 67% of men and 62% of women are overweight. Further, 28% of men and 34% of women are considered obese with 5-7% in the morbidly obese category. The overweight population represents a large segment of the surgical caseload and presents significant challenges to the anesthesiologist, particularly during endotracheal intubation.

One of the most important tasks of an anesthesiologist is the management of the patient's airway during the administration of anesthesia. In order to maximize visualization of the larynx during endotracheal intubation, the anesthesiologist must place the patient's head and upper back in the "sniffing" position to properly align the oropharyngeal, laryngeal, and tracheal axes. The obese patient presents a challenge for proper alignment because of excess tissue in the upper back, neck, and oral pharynx.

Physiological changes occurring during pregnancy further complicate airway management in the pregnant patient. Fluid retention, weight gain, enlarged breasts, incompetent lower esophageal-gastric sphincter and friable mucosal tissue all add to the difficulty of visualization of the larynx during endotracheal intubation. Accordingly, failed intubation during anesthetic induction occurs almost ten times more frequently in pregnant patients than in non-pregnant surgical patients.

Endotracheal intubation is a medical procedure in which an endotracheal tube is inserted through the oral cavity into the trachea to provide controlled or spontaneous ventilation and to protect the lungs from gastric acid contamination. This protection is provided by a balloon on the tip of the tube that is inflated when the tube is in the proper location above the carina. Prior to the induction of anesthesia, a pillow or pad is placed under the patient's head to elevate the head above the shoulders in the "sniffing" position. This "sniffing" position helps align the oropharyngeal, laryngeal, and tracheal axes and facilitates the placement of the endotracheal tube into the trachea. After anesthetic induction, the anesthesiologist or nurse anesthetist places a laryngoscope blade into the mouth, the tongue and jaw are slightly elevated, the trachea and vocal cords are visualized and the endotracheal tube is introduced through the mouth into the trachea. The laryngoscope blade is then removed, the tube balloon is inflated, and proper ventilation of the lungs is confirmed. This procedure is typically carried out in the operating room. However, it is also performed in emergency situations outside of the operating room such as the emergency room, hospital room, or at the scene of accidents.

When the obese patient is supine on the operating table, a standard pillow or pad does not elevate the neck and head adequately above the shoulders to provide the necessary "sniffing" position. As a result, a known current regimen involves placing several layers of blankets under the upper back, neck, and head of the patient to create a ramp in order to elevate an obese patient's upper body so that the pinna of the ear and the sternum are in the same horizontal plane. This may require ten to fifteen blankets in the morbidly obese patient. Although this method of support is efficacious, there are several disadvantages. First, health care professionals are put at risk for injuries as a result of lifting the obese patient for pre-induction blanket positioning as well as lifting the patient to remove the blankets after intubation. Blankets must also be removed so that the patient's shoulders and arms are level with each other in order to minimize the risk of a brachial plexus stretch injury. In addition, the endotracheal tube may become dislodged while lifting the patient to remove the blankets. Further, the cost of laundering the large number of blankets used in each case is significant. Moreover, it is difficult and time-consuming to adjust the blanket placement for proper positioning after the patient is on the operating room table.

The pregnant patient undergoing a Cesarean section, or other surgical procedure, presents two major concerns to the anesthesiologist. In addition to the physiological changes that occur during pregnancy that increase the risk of a difficult intubation, the enlarged, gravid uterus can partially obstruct the venous return to the heart by compressing the inferior vena cava if the patient is left in the supine position on the operating room table. This syndrome can cause a 25-30% decrease in cardiac output resulting in maternal hypotension and decreased blood flow to the fetus. In order to alleviate the decrease in venous return, the right side of the pregnant patient is tilted up 1530 degrees to the left side of the patient to move the uterus away from the inferior vena cava. Presently, this "left lateral tilt" is obtained by either placing a liter saline bag under the right side or manually inflating a bladder bag under the patient's right side. The former method is non-adjustable and does not allow adequate tilt in large patients. The latter method is burdensome and time-consuming during the critical part of pre-induction preparation and oxygenation.

Accordingly, there is a need for an improved device that allows for specific adjustments in the position of a patient's upper back, neck and head to obtain the best alignment of the oropharyngeal, laryngeal, and tracheal axes in obese and pregnant patients so that endotracheal intubation can be performed quickly with minimal trauma to patients. There also exists a need for a device that prevents injury to health care professionals performing endotracheal intubation by eliminating the need to lift obese patients before and after induction of anesthesia. There is a further need for a device that allows anesthesiologists to quickly and adequately obtain a left lateral tilt in pregnant patients irrespective of the patient's anatomy.

BRIEF SUMMARY OF THE INVENTION

It is an object of the present invention to provide an improved device and method for facilitating endotracheal intubation in obese and pregnant patients by providing a device configured to adjust the patient's upper body to permit alignment of the patient's ear and sternum in the same horizontal plane, a position that produces the best alignment of the oropharyngeal, laryngeal, and tracheal axes for efficient intubation of the trachea during the critical period of anesthetic induction. It is yet another object of the present invention to provide a method and device that allows a quick and efficient left lateral tilt of the uterus in pregnant patients undergoing a surgical procedure, such as a Cesarean section.

These and other objects of the present invention are accomplished by providing an apparatus for aligning the oropharyngeal, laryngeal, and tracheal axes in the obese and/or pregnant patient. The apparatus includes a plurality of inflatable sections configured to adjust the patient's upper body such that the patient's ear and sternum are aligned in the same horizontal plane. The inflatable sections are independently inflatable and deflatable with respect to one another or may be grouped so that groups of inflatable section are independently inflatable and deflatable with respect to other groups. The apparatus also includes an anchoring means attached to at least one of the plurality of inflatable sections. The anchoring means is positioned under the patient and is designed to allow the patient's weight to anchor the apparatus in place. The anchoring means is optionally configured with an inflatable cylinder or pocket on the right side so that it can produce a left lateral tilt of a pregnant patient during a surgical procedure. The apparatus further includes an air system that is selectively connected to one or more of the inflatable sections for inflating and deflating the inflatable sections independently of one another. The present invention also includes a method for aligning the patient's oropharyngeal, laryngeal, and tracheal axes.

BRIEF DESCRIPTION OF THE DRAWINGS

FIG. 10 is an illustration of an obese patient positioned on the apparatus in accordance with the present invention, illustrating proper inflation of the apparatus such that the pinna of the ear and sternum (P-S) are in the same horizontal plane.

DETAILED DESCRIPTION OF THE INVENTION

Figure 1:
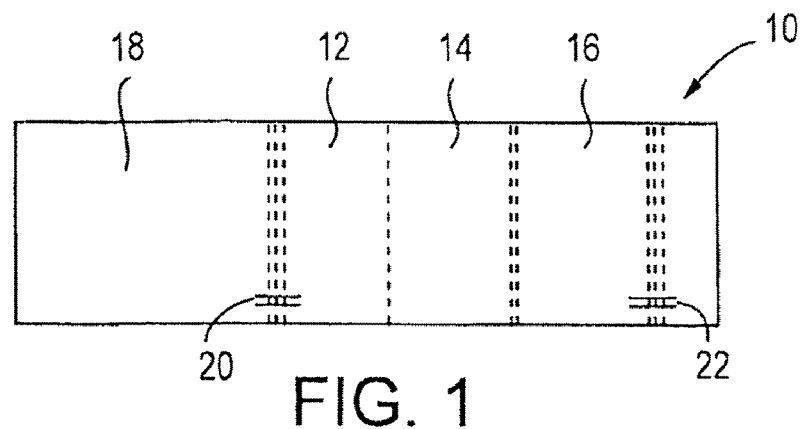
FIG. 1 is a top view of one embodiment of the apparatus of the present invention.

The apparatus and method of the present invention as described and illustrated in FIGS. 1 through 11 overcome the disadvantages set forth above. Referring to FIG. 1, the apparatus in accordance with the present invention is constructed of high-strength plastic or other types of polymers that impart strength to the pillow like structure. The apparatus 10 (referred to hereinafter as a "pillow") is preferably about 16 to 18 inches wide and preferable about 20 to 24 inches long. This measurement may be varied depending on whether the patient is an adult, male or female, or a pediatric patient. Pillow 10 comprises several sections 12, 14 and 16 that are independently inflatable/deflatable using pressurized air delivered through inlets/outlets 20 and 22. In one embodiment of the present invention three inflatable sections 12, 14 and 16 are present. In an alternative embodiment, additional sections may be added depending on whether pillow 10 will be used with a male, female or pediatric patient. An optional anchoring means 18 may be included to anchor pillow 10 using the patient's body weight thus preventing pillow 10 from being dislodged or otherwise moved away from the patient's body. Anchoring means 18 can be configured as an extended tail section, fastenable straps, weighted portion, and other such means known by those skilled in the art. Anchoring means 18 may be attached to at least one of the inflatable sections or may be removably coupled to at least one of the inflatable sections with means such as a zipper, Velcro and the like. First and second inflatable sections 12, 14 are grouped together and inflated and deflated via common inlet/outlet 20 by air system 50, hereinafter described. Third inflatable section 16 is inflated and deflated via inlet/outlet 22, which is connected to air system 50. First and second sections 12, 14 and third section 16 are independently inflatable and deflatable.

Figure 2:
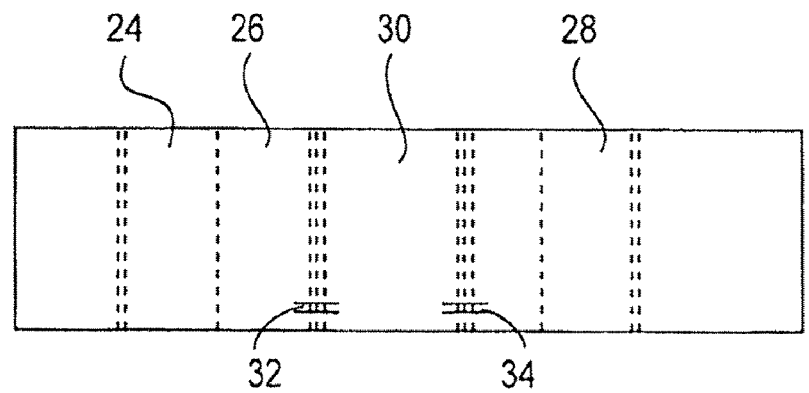
FIG. 2 is an alternative embodiment of the apparatus depicted in FIG. 1.

As those skilled in the art can appreciate, the number of inflatable sections and how they are grouped together for inflation and deflation purposes can be as varied as the differences in human anatomy dictate. For example and referring to FIGS. 2 and 3, there are shown additional embodiments of pillow 10 where additional inflatable sections have been added. Referring to FIG. 2, inflatable sections 24 and 26 are separated from inflatable section 28 by a no fill section 30. No fill section 30 is used to isolate elevation to the patient's abdominal area rather than elevating the entire side of the patient. Use of no fill section 30 is advantageous when using pillow 10 to facilitate intubation of pregnant patients as discussed in detail below. Inflatable sections 24 and 26 are inflated and deflated via inlet/outlet 32 that is connected to air system 50. Inflatable section 28 is inflated and deflated via inlet/outlet 34 that is connected to air system 50. Inflation and deflation of sections 24, 26 are independent of the inflation and deflation of section 28.

Figure 3:
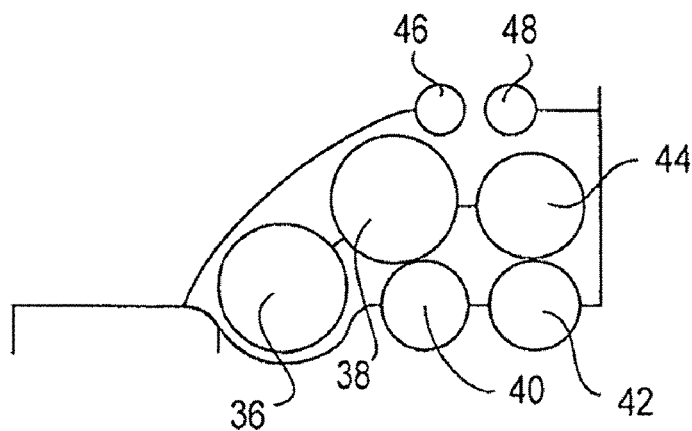
FIG. 3 is a cross section of an illustration of the apparatus in accordance with the present invention.
Figure 4:
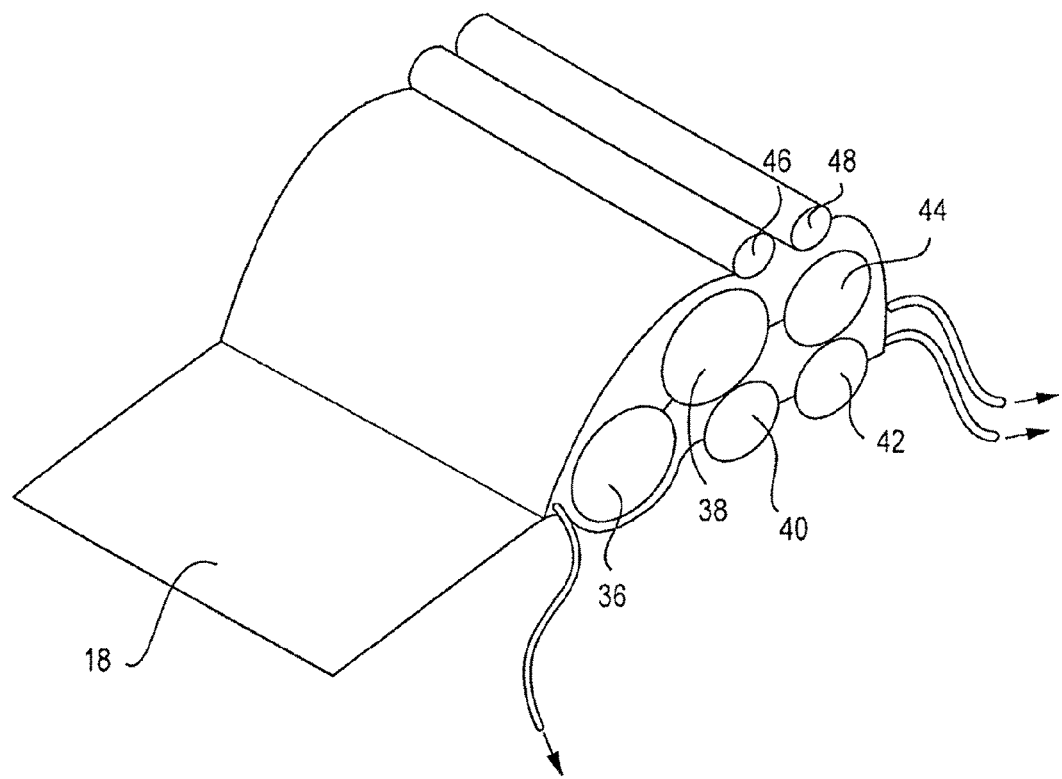
FIG. 4 is a perspective side view of the apparatus in accordance with the present invention.

Referring now to FIGS. 3 and 4, an exemplary embodiment of pillow 10 in accordance with the present invention is depicted. Pillow 10 includes first and second back support inflatable sections 36 and 38, first and second base support inflatable sections 40 and 42, a head tilt adjustment inflatable section 44, and first and second head rest inflatable sections 46 and 48, grouped together as noted for purposes of inflation and deflation. Back support inflatable sections 36 and 38 are adjacent anchoring means 18 and provide immediate support for a patient's upper back. Base support inflatable sections 40 and 42 are placed at the bottom of pillow 10 in order to provide support for back support inflatable sections 36 and 38, head tilt adjustment inflatable section 44, and head rest inflatable sections 46 and 48. Head rest inflatable sections 46 and 48 are placed at the top of pillow 10 such that a patient's head may be placed on them. Head tilt adjustment inflatable section 44 is between head rest inflatable sections 46 and 48 and base support inflatable sections 40 and 42 and can be inflated and/or deflated until proper alignment of the pinna of the patient's ear and sternum in the same horizontal plane is obtained thus resulting in proper alignment of the patient's oropharyngeal, laryngeal, and trachealaxes in preparation for intubation.

Figure 5:
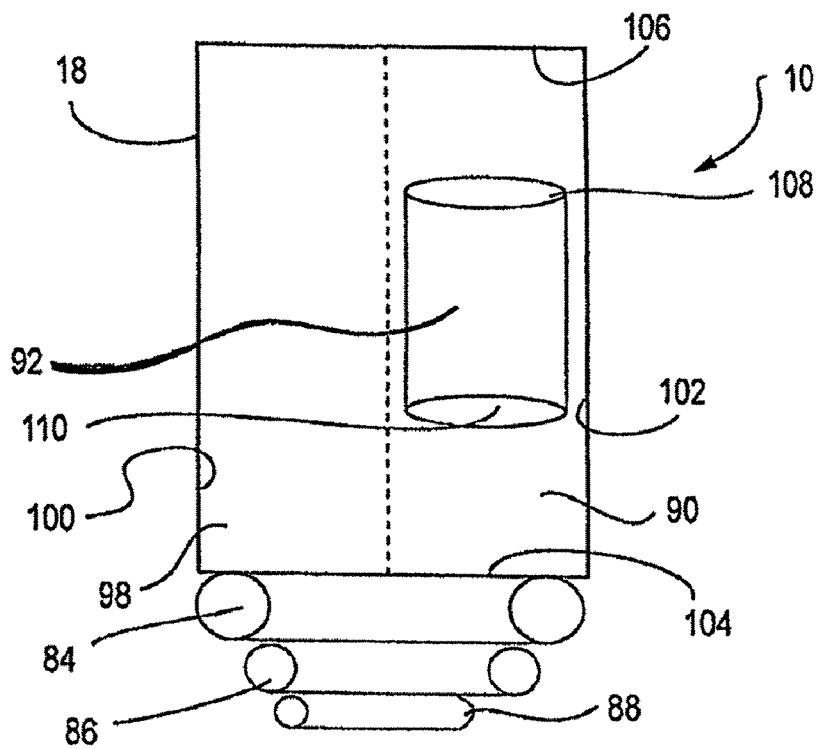
FIG. 5 is a top plan view of the apparatus in accordance with the present invention, viewed from the perspective of an anesthesiologist at the head of the operating table, including an independently inflatable cylinder.
Figure 6:
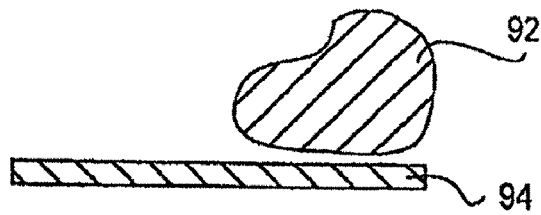
FIG. 6 is a cross sectional view of the cylinder of FIG. 5.
Figure 7:
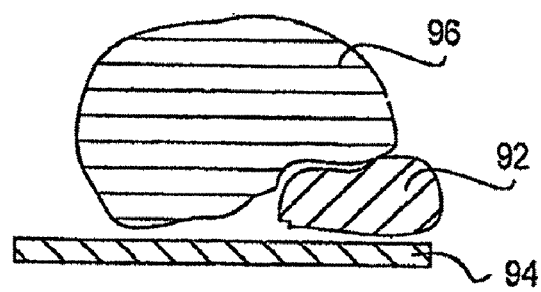
FIG. 7 is a cross sectional view of the cylinder of FIG. 6 in accordance with the present invention illustrating a pregnant patient's torso positioned thereupon.

Referring now to FIG. 5, an alternative embodiment of pillow 10 in accordance with the present invention is shown. Pillow 10 includes a plurality of inflatable sections 84, 86, 88 that are positioned under the patient's head and shoulders. Pillow 10 includes an anchoring means 18 optionally divided by stitching into left and right side sections 90, 98. Right side section 98 includes an independently inflatable cylinder or pocket 92 therewithin. Each side section 90, 98 of pillow 10 is preferably about 28 inches along its longitudinal sides 100, 102 and preferably about 16 inches along its latitudinal sides 104, 106. Referring to FIG. 6, independently inflatable cylinder or pocket 92 is depicted in cross section supported by operating table 94. In an alternative embodiment, an inflatable cylinder 92 may be separate from anchoring means 18, i.e. not enclosed therewithin, and via a quick connect/disconnect (not shown) may still be connected to air system 50. Cylinder 92 of this alternate embodiment is placed under anchoring means 18 of pillow 10 and is supported by operating table 94 in FIG. 6. Those skilled in the art can therefore appreciate that such a separate cylinder could thus be configured in various shapes and sizes depending on the size of the pregnant patient being treated and could be quickly changed out to suit the size of the patient. FIG. 7 illustrates the positioning of a pregnant patient 96 on cylinder 92, where cylinder 92 is supported by operating table 94.

Independently inflatable cylinder or pocket 92 positioned within anchoring means 18 can also be configured of various shapes and sizes depending on the size of the patient being treated. Regardless of the shape or size, independently inflatable cylinder or pocket 92 is generally positioned on right side 98 of pillow 10 as depicted in FIG. 5 so that, when inflated, it provides left uterine displacement. In one embodiment of the present invention, independently inflatable section 92 is sized and positioned such that its first longitudinal end 108 is about 5 inches from first inflatable section 84 and its second longitudinal end 110 is approximately 5 inches from latitudinal side 104. The specific longitudinal placement of independently inflatable section 92, however, can vary depending on the size of the patient.

Figure 8:
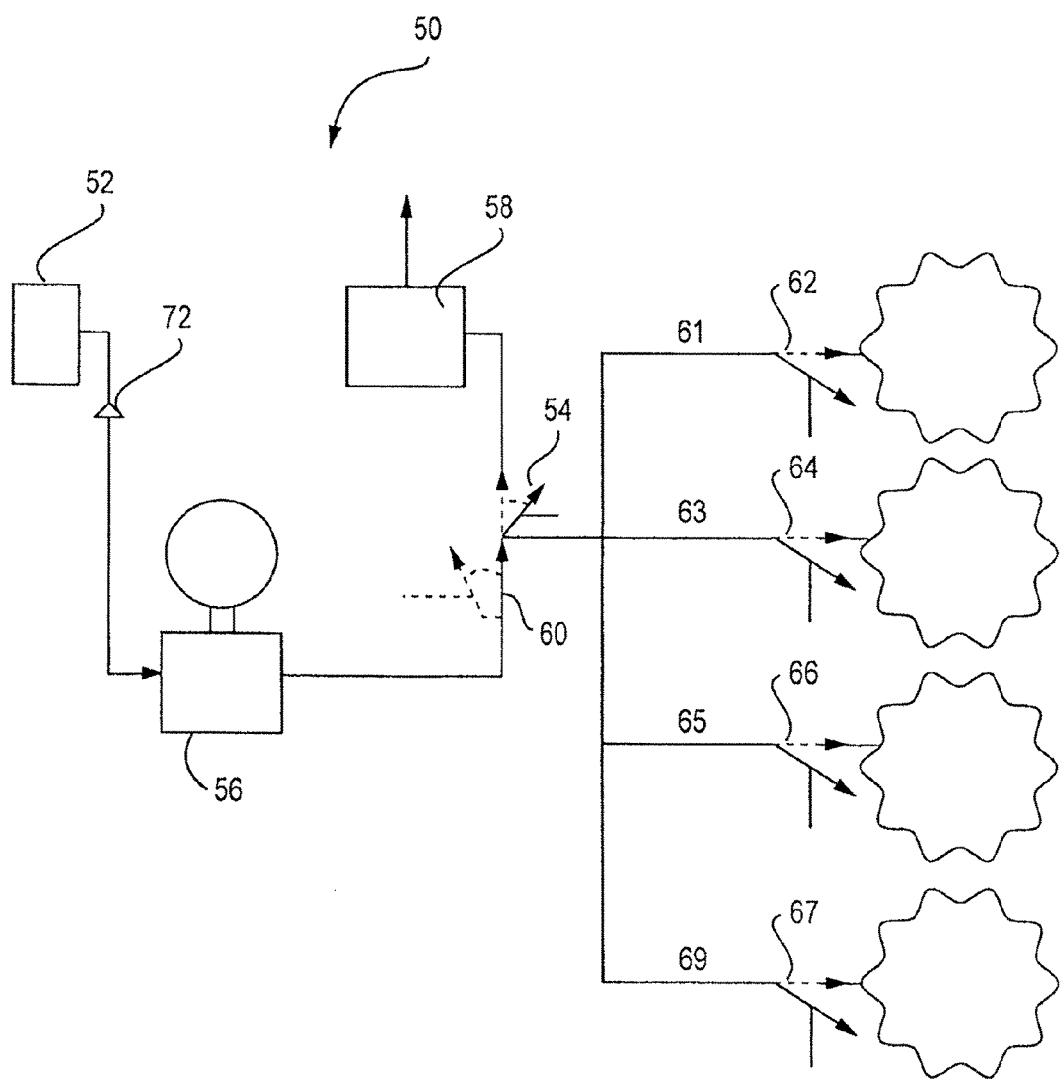
FIG. 8 is a schematic of an air system in accordance with the present invention.

Referring now to FIG. 8, there is shown an exemplary air system 50 including a pneumatic valve assembly for inflating and deflating the various sections of pillow 10 in accordance with the present invention. Air system 50 can be operated to either inflate or deflate independently groupings of inflatable sections of pillow 10 until the best anatomical position for endotracheal intubation of the patient is achieved. Those skilled in the art can appreciate that the number of sections air system 50 is designed to inflate is not limited to the number depicted in FIG. 8, which simply illustrates the operation of an exemplary air system. Those skilled in the art will also appreciate that air system 50 may be hard plumbed in the operating room and connected directly to the compressed air line of the hospital or may be designed as a portable system with a portable canister of compressed air.

When air system 50 is set for inflation, deflate valve 54 is closed in the closed position and inflate valve 60 is set to the open position. In one embodiment of air system 50 in accordance with the present invention, hospital compressed air supply 52 is routed through air input 72, which is provided with a special medical grade quick disconnect fitting to allow for quick disconnect of the system in the event that a pressure regulator 56 malfunctions. The compressed air is then routed through pressure regulator 56 to ensure proper inflation pressure and to ensure that pillow 10 does not become over inflated. Regulator 56 may be an adjustable type pressure regulator allowing an operator to adjust the maximum allowable air line pressure. Alternatively, pressure regulator 56 may be a fixed pressure regulator in which the maximum air line pressure is fixed at a predetermined air pressure. On/off switches 62, 64, 66 and 67 are either on or off depending on which grouping of inflatable pillow sections, or which individual inflatable pillow sections, are being inflated or deflated. For example, when base support grouping of inflatable sections 40 and 42 and head rest grouping of inflatable sections 46 and 48 are to be inflated, on/off switch 62 is placed in the on position. When head tilt adjustment grouping of inflatable sections 44 are to be inflated, on/off switch 64 is placed in the on position. When back support inflatable sections 36 and 38 are to be inflated, on/off switch 66 is placed in the on position.

Conversely, when air system 50 is set for deflation, inflate valve 60 is set to the closed position and deflate valve 54 is set to the open position. A vacuum generator 58 is operated to draw air out of the inflatable pillows. Vacuum generator 58 uses compressed air to create a vacuum allowing for quicker deflation of the various groupings of inflatable sections. The grouping of inflatable sections can be selectively deflated by turning on/off switches 62, 64 and 66 to the on position as previously described for inflation. While those skilled in the art will recognize that it is advantageous to use vacuum generator 58 for active deflation of the inflatable sections, the use of vacuum generator 58 is optional as the patient's weight will also cause deflation when valve 60 is closed and valve 54 is open to ambient air. Those skilled in the art will also appreciate that the number of inflate and deflate valves and the configuration of air system 50 can vary from that depicted in FIG. 8 and still fall within the spirit of the present invention.

Figure 9:
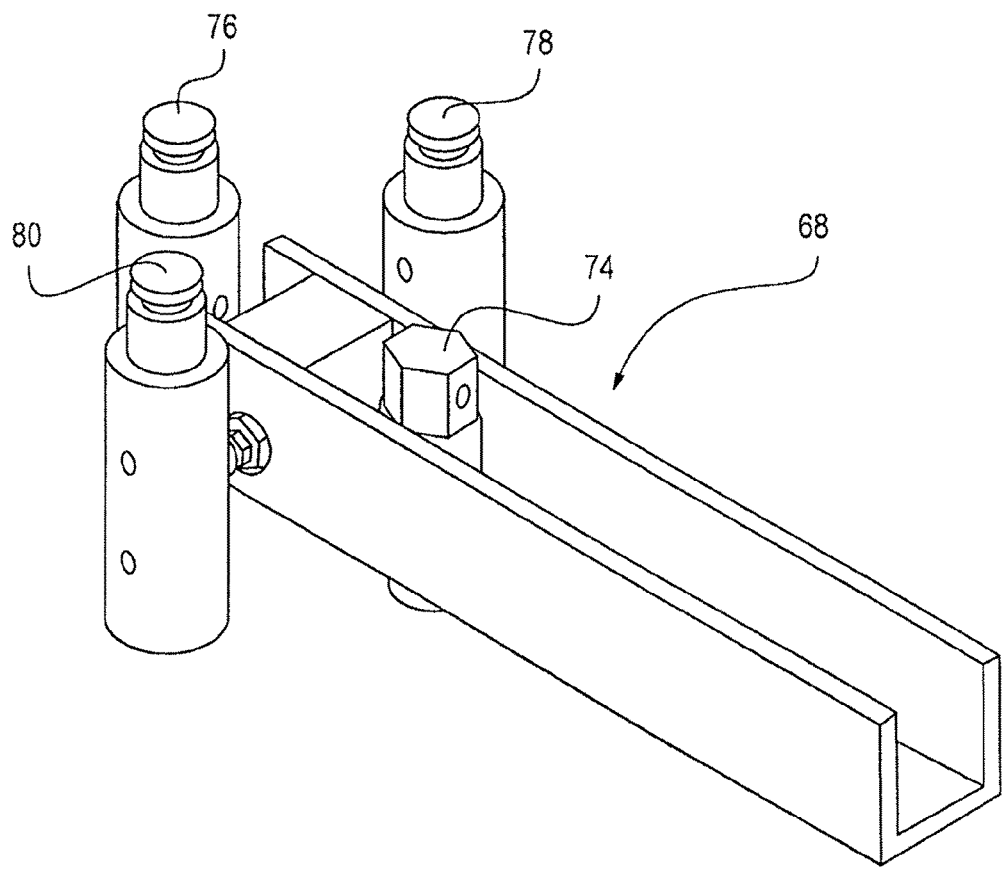
FIG. 9 is a perspective side view of a push button valve assembly used to inflate/deflate the apparatus in accordance with the present invention.

There is depicted in FIG. 9, according to one embodiment of the present invention, an easy to use hand-held push button valve assembly 68 that is operably connected to air system 50 but allows for easy hand-held manipulation of the inflation and deflation process by the anesthesiologist. Valve assembly 68 includes a momentary push button valve 74 that allows for rapid inflation of all inflatable pillow sections when placed in a first position and rapid deflation of all inflatable pillow sections when placed in a second position. The push button valve assembly 68 also includes three or more momentary push button valves 76, 78 and 80 for independently controlling the inflation and deflation of a particular grouping of inflatable pillow sections. In a first position, buttons 76, 78 and 80 independently allow air fill of inflatable sections individually or in any group combination. In a second position, the inflatable sections are deflated individually or in any group combination. A fourth momentary push button valve (not shown) can optionally be added to control inflation and deflation of cylinder or pocket 92 in anchoring means 18, or a separate cylinder placed under anchoring means 18. Alternatively, separate cylinder 92, whether positioned within anchoring means 18 or separated from anchoring means 18, can be controlled by a momentary push button valve that controls one of the groupings of inflatable pillow sections.

Now that each component of the present invention has been discussed, the following discussion describes the use of use of the pillow 10 in operation. Referring to FIGS. 8 and 10, the upper back of a patient is placed on back support inflatable sections 36 and 38 such that his/her head is positioned on head rest inflatable sections 46 and 48 and his/her mid to lower back is positioned on anchoring means 18 in order to hold the pillow 10 in place. Preferably, pillow 10 is partially inflated on the operating table before placing the patient thereon. Alternatively, it would not be outside the scope of the present invention if pillow 10 was completely deflated before placing the patient on it. After the patient is positioned on pillow 10, back support inflatable sections 36 and 38, base support inflatable sections 40 and 42 and head rest inflatable sections 46 and 48 are slowly inflated to properly align the upper body so that the pinna and sternum are in the same horizontal plane. Back support inflatable sections 36 and 38, base support inflatable sections 40 and 42 and head rest inflatable sections 46 and 48 are inflated by setting deflate valve 54 to the closed position and inflate valve 60 to the open position. On/off switch 62 for base support inflatable sections 40 and 42 and head rest inflatable sections 46 and 48 is placed in the on position. On/off switch 66 for back support inflatable sections 36 and 38 is placed in the on position. Air is supplied to pillow 10 until the "sniffing" position 82 is achieved.

When necessary, back support inflatable sections 36 and 38, base support inflatable sections 40 and 42 and head rest inflatable sections 46 and 48 are deflated by leaving on/off switches 62 and 66 in the on, setting inflate valve 60 to the closed position, setting deflate valve 54 to the open position, and activating vacuum generator 58 via an easy to access manual switch (not shown) to expel the air. During inflation and deflation, base support inflatable sections 40 and 42 and head rest inflatable sections 46 and 48 are inflated or deflated by placing the on/off switch 62 in the on position. Similarly, back support inflatable sections 36 and 38 are independently inflated or deflated by placing on/off switch 66 in the on position. Air is delivered to inflatable pillow sections via air lines 61, 63, and 65. In this manner, all of the inflatable sections can be inflated or deflated independent of one another to achieve the correct anatomical position of supporting the patient's upper back, shoulders, neck and head to align the pinna of the ear and sternum in the same horizontal plane.

In order to place the patient in the "sniffing" position 82, the healthcare professional adjusts the pressure in head tilt adjustment section 44 by either inflating or deflating it. The healthcare professional can inflate head tilt adjustment inflatable section 44 by setting deflate valve 54 to the closed position, setting inflate valve 60 to the open position, and placing on/off switch 64 for head tilt adjustment inflatable section 44 in the on position. Head tilt adjustment inflatable section 44 is deflatable by leaving on/off switch 64 in the on position, setting inflate valve 60 to the closed position, setting deflate valve 54 to the open position, and activating vacuum generator 58 to expel the air.

Pillow 10 of the present invention may also be used with a pregnant patient to achieve proper left lateral tilt and is best described by referring to FIGS. 5, 6, and 7. The upper back of a pregnant patient is placed on inflatable section 84 with the patient's neck and head positioned on inflatable sections 86, 88, respectively. The patient's mid to lower back are positioned on anchoring means 18 in order to hold pillow 10 in place. Inflatable cylinder 92 is positioned under the patient's right side as she lies on pillow 10. Inflatable sections of pillow 10 and/or independently inflatable cylinder or pocket 92 are preferably partially inflated before placing the patient on pillow 10. Alternatively, pillow 10 and/or independently inflatable cylinder or pocket 92 can be completely deflated before placing the patient on it. However, before a healthcare professional attempts to properly align a patient's oropharyngeal, laryngeal, and trachealaxes, inflatable cylinder or pocket 92 must be inflated such that the patient is in the left lateral tilt position as best seen in FIG. 7. Referring again to FIG. 8, independently inflatable cylinder 92 is inflated by setting deflate valve 54 to the closed position and inflate valve 60 to the open position. On/off switch 67 for independently inflatable cylinder 92 is placed in the on position. Air is supplied to cylinder 92 via air line 69 until the patient is placed in the left lateral tilt position. The remaining inflatable sections 84, 86, 88 are inflated and deflated in the manner previously discussed in order to properly align the pregnant patient's oropharyngeal, laryngeal, and trachealaxes before intubation.

The induction of anesthesia in obese and pregnant patients carries significant risk of morbidity and mortality secondary to problems faced by health care professionals in managing the airways of these patients. Pillow 10 of the present invention allows health care professionals to rapidly and effectively place patients in the proper position to ease placement of endotracheal tubes and minimize risks to patients. The invention has been described in connection with the best mode now known to the applicant inventors. The invention is not to be limited to the disclosed embodiment. Rather, the invention covers all of various modifications and equivalent arrangements included within the spirit and scope of the disclosure.

What is claimed is:

1. A method of positioning an obese and/or pregnant patient for endotracheal intubation, the method comprising:
    positioning an upper back of the patient on an independently inflatable and deflatable back support section of a pillow, the back support section including a first portion and a second portion that are inflatable together via a single common air inlet/outlet;
    positioning a head of the patient on an independently inflatable and deflatable head rest section of the pillow;
    inflating the back support section;
    inflating the head rest section;
    inflating an independently inflatable and deflatable base support section of the pillow in order to adjust an elevation of the head rest section and the second portion of the inflated back support section without adjusting an elevation of the first portion of the back support section, the base support section being located beneath both the second portion of the back support section and the head rest section; and
    aligning a pinna of an ear of the patient with a sternum of the patient in the same horizontal plane, when the patient's upper back is positioned on the inflated back support section and the patient's head is positioned on the inflated head rest section, by adjusting a pressure in an independently inflatable and deflatable head tilt adjustment section of the pillow, the head tilt adjustment section being located above the base support section and beneath the head rest section.

2. The method of claim 1, wherein inflating each of the back support section, the head rest section and the head tilt adjustment section comprises setting an inflate valve in an on position and setting an on/off switch of each section in an on position.

3. The method of claim 2, wherein setting the inflate valve comprises pushing a button, and setting each of the on/off switches comprises pushing a button for each of the on/off switches.

4. The method of claim 1, further comprising deflating at least one of the back support section, the head rest section, the base support section and the head tilt adjustment section, after inflating each of the sections.

5. The method of claim 4, wherein deflating at least one of the back support section, the head rest section, the base support section and the head tilt adjustment section comprises setting a deflate valve in an on position and setting an on/off switch of the at least one section in an on position.

6. The method of claim 4, wherein setting the deflate valve comprises pushing a button, and setting each of the on/off switches comprises pushing a button for each of the on/off switches.

7. The method of claim 1, wherein the back support section, the head rest section and the base support section are all inflated simultaneously.

8. The method of claim 1, further comprising:
connecting an air system of the pillow to a compressed air source and setting an inflate valve of the air system in an open position in order to inflate the back support section, the head rest section and the base support section, and to adjust the pressure in the head tilt adjustment section; and
wherein inflating the back support section comprises setting a first on/off switch of the air system in an on position; and inflating, simultaneously, the head rest section and the base support section comprises setting a second on/off switch of the air system in an on position.

9. A method of positioning an obese and/or pregnant patient for endotracheal intubation, the method comprising:
positioning a mid to lower back of the patient on an extended tail section of a pillow;
positioning an upper back of the patient on an independently inflatable and deflatable back support section of the pillow;
positioning a head of the patient on an independently inflatable and deflatable head rest section of the pillow;
inflating the back support section;
inflating the head rest section;
adjusting an elevation of the head rest section and only a portion of the back support section, by inflating the head rest section and an independently inflatable and deflatable base support section of the pillow; and
aligning a pinna of an ear of the patient with a sternum of the patient, when the patient's mid to lower back is positioned on the extended tail section, the patient's upper back is positioned on the inflated back support section, and the patient's head is positioned on the inflated head rest section, by adjusting a pressure in an independently inflatable and deflatable head tilt adjustment section of the pillow.

10. The method of claim 9, further comprising:
connecting an air system of the pillow to a compressed air source and setting an inflate valve of the air system in an open position in order to inflate the back support section, the head rest section and the base support section, and to adjust the pressure in the head tilt adjustment section; and
wherein inflating the cylinder comprises setting a first on/off switch of the air system in an on position;
inflating the back support section comprises setting a second on/off switch of the air system in an on position; and
inflating, simultaneously, the head rest section and the base support section comprises setting a third on/off switch of the air system in an on position.

11. The method of claim 10, further comprising setting the inflate valve to a closed position and then setting a deflate valve of the connected air system to an open position, in order to deflate one or more of the cylinder, the back support section and the head rest and base support sections, and to adjust the pressure in the head tilt adjustment section.

12. The method of claim 9, wherein the back support section and the head rest and base support sections are inflated simultaneously.

* * * * *